United States Patent
Gedon et al.

(10) Patent No.: US 6,433,206 B1
(45) Date of Patent: Aug. 13, 2002

(54) PROCESS FOR PREPARING SILYLORGANOMERCAPTANS

(75) Inventors: Steven C. Gedon, Williamstown; Melinda Hale, Belmont, both of WV (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/012,286

(22) Filed: Nov. 15, 2001

(51) Int. Cl.$^7$ .................................................. C07R 7/08
(52) U.S. Cl. ........................................................ 556/627
(58) Field of Search ............................................ 556/427

(56) References Cited

U.S. PATENT DOCUMENTS

| | | | |
|---|---|---|---|
| 3,345,393 A | * 10/1967 | Simmler et al. | ............ 556/427 |
| 3,350,437 A | * 10/1967 | Simmler et al. | ............ 556/427 |
| 3,957,844 A | * 5/1976 | Mui | ........................... 556/427 |
| 4,072,701 A | 2/1978 | Pletka et al. | |
| 4,408,064 A | 10/1983 | Schwarz et al. | |
| 4,560,679 A | * 12/1985 | Toyoshima et al. | ...... 556/427 X |
| 5,466,848 A | 11/1995 | Childress | |
| 5,489,701 A | 2/1996 | Childress et al. | |
| 5,596,116 A | 1/1997 | Childress et al. | |
| 5,663,395 A | 9/1997 | Gobel et al. | |
| 5,663,396 A | 9/1997 | Musleve et al. | |
| 5,859,275 A | 1/1999 | Munzenberg et al. | |
| 5,892,085 A | 4/1999 | Munzenberg et al. | |
| 5,965,760 A | * 10/1999 | Michel et al. | ............... 556/427 |
| 6,147,241 A | 11/2000 | Michel et al. | |
| 6,147,242 A | 11/2000 | Batz-Sohn | |
| 6,153,782 A | * 11/2000 | Krauter et al. | ........... 556/427 X |
| 6,242,652 B1 | 6/2001 | Bennet | |
| 6,274,755 B1 | 8/2001 | Munzenberg et al. | |

FOREIGN PATENT DOCUMENTS

| | | |
|---|---|---|
| DE | 1903968 | 8/1970 |
| EP | 0649837 | 10/1994 |
| FR | 2008331 | 1/1970 |
| NL | 6402424 | 3/1964 |

OTHER PUBLICATIONS

Bergmann et al. Ber. Dtsch.Chem. Ges. 63,987 (1930) –[No English translation available–background information only].
Broadbent et al., J. Am. Chem.Soc., 76, 1519 (1954).
Calaise et al. J. of Cat., 144, 160–174 (1993).
CA, 53, 17978a (1959).
CA, 53, 21763f (1959).
CA, 54, 2153e (1960).
CA, 54, 19466 c and g (1960).

* cited by examiner

*Primary Examiner*—Paul F. Shaver
(74) *Attorney, Agent, or Firm*—Michael P. Dilworth

(57) ABSTRACT

A process for preparing an organomercaptan is provided which comprises reacting a sulfide of the general formula (I)

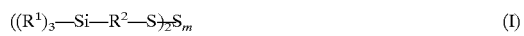

in which each $R^1$ is the same or different alkyl group of up to about 6 carbon atoms, aryl group of up to about 10 carbon atoms or alkoxy group of up to about 6 carbon atoms, or at least two of $R^1$ and the silicon atom to which they are bonded form a ring system having up to about 12 ring members with no ethylenic unsaturation and optionally containing one or more heteroatoms selected from the group consisting of oxygen, sulfur and nitrogen, each $R^2$ is the same or different divalent hydrocarbon group containing no ethylenic unsaturation and having up to about 20 carbon atoms and m is 0 to about 8, with hydrogen under hydrogenolysis conditions in the presence of a catalytically effective amount of Group VIII metal catalyst and in the presence of a catalyst poisoning inhibiting amount of a catalyst poisoning inhibitory agent selected from the group consisting of water, except where the mercaptan product contains at least one hydrolyzable silane group, alkanol of from 1 to about 6 carbon atoms, hydrogen sulfide and mixtures thereof to provide organomercaptan product of the general formula (II)

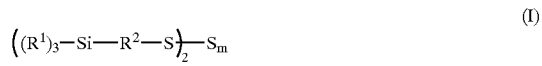

in which $R^1$ and $R^2$ each has one of the aforestated meanings.

20 Claims, No Drawings

PROCESS FOR PREPARING SILYLORGANOMERCAPTANS

BACKGROUND OF THE INVENTION

This invention relates to the field of processes for preparing organomercaptans. More particularly, the present invention describes a process for preparing organomercaptan by the catalyzed hydrogenolysis of a disulfide, trisulfide, and/or polysulfide.

U.S. Pat. No. 6,147,242 describes a process for preparing 3-mercaptopropyl-triethoxysilane by the homolytic cleavage of the corresponding bis-disulfide. The method involves reacting a bis-silylalkylsulfide with an alkali metal and a chlorosilane to provide a silylalkylsulfanylsilane intermediate which is recovered and thereafter hydrolyzed in the presence of refluxing aqueous alcohol to the desired mercaptoalkylsilane. The foregoing method is subject to several disadvantages including its use of a chlorosilane which is expensive, the necessity to filter and dispose of hazardous alkali metal salt, and the need to isolate a silylalkylsulfanylsilane intermediate prior to the hydrolysis step.

Itabashi, CA 54, 2153e (1960), CA, 54, 19466c (1960) and CA, 54, 19466g (1960), describes the reaction of various disulfides with hydrogen over molybdenum (VI) sulfide catalyst at 130°–140° C. and 10.7 MPa hydrogen pressure resulting in the hydrogenolysis of the disulfides at the S—S linkage to provide the corresponding organomercaptans in high yields. The high catalyst loading for the reaction (approximately 5 weight percent) and the high cost of the catalyst both add significantly to the expense of this preparative method. A similar process described by Broadbent et al., *J. Am. Chem. Soc.*, 76, 1519 (1954), provides thiophenol quantitatively by hydrogenolysis of diphenyl disulfide over $Re_2S_7$ in 2-methoxyethanol at 165° to 195° C. and 15 MPa hydrogen pressure. At these high temperatures, however, subsequent de-sulfurization exclusively results in the saturated hydrocarbon or aromatic substrate.

In general, precious metal and base metal catalysts have found little application in the selective cleavage of the S—S bond due to the known poisoning effect of the resulting sulfides. In the few cases that have been reported, however, palladium catalysts, which are generally known for their resistance to catalyst poisons, have been the most reactive and have achieved the highest yields. The most striking example of this is the hydrogenolysis of methyl cystine to methyl cysteine in the presence of 25 weight percent of palladium catalyst in aqueous acid at room temperature and atmospheric pressure (Bergmann et. al. *Ber. Dtsch. Chem. Ges.* 63,987 (1930)). The necessity to use an unusually high loading of expensive palladium catalyst, however, precludes its use in all but a limited number of research applications.

Patent EP 649,837 discloses a process for the preparation of methyl mercaptan from the corresponding dimethyl disulfide using a transition metal catalyst which requires a sulfidation pretreatment with a hydrogen sulfide/hydrogen mixture (containing 15 mole percent hydrogen sulfide) at an hourly flow rate of 2 liters mixture per gram of catalyst at 400° C. for 4 hours. The selectivity and the yield of the process are reported to be improved when the reaction is conducted in the presence of either water or hydrogen sulfide at a concentration of 0.1 to 15 weight percent with respect to the disulfide.

Other catalyst systems have also been reported that are based on transition metal sulfides since the sulfide phases are believed to be more resistant to poisoning by sulfur-containing molecules (Calais et al. *J of Cat.*, 144, 160–174 (1993)). The use of platinum sulfides (Dutch Patent Application No. 6,402,424) for the reduction of diphenyl disulfide to phenyl mercaptan as well as the sulfides of Raney Ni and Raney Co (French Patent Application No. 2,008,331) and Ru, Rh, Pt, Ir, and Pd (German Patent Application No. DE 1,903,968) require relatively high hydrogen pressures, typically in excess of 5–10 MPa.

SUMMARY OF THE INVENTION

In accordance with the present invention, a process is provided for preparing an organomercaptan which comprises reacting a sulfide of the general formula (I)

in which each $R^1$ is the same or different alkyl group of up to about 6 carbon atoms, aryl group of up to about 10 carbon atoms or alkoxy group of up to about 6 carbon atoms, or at least two of $R^1$ and the silicon atom to which they are bonded form a ring system having up to about 12 members and containing no ethylenic unsaturation, and optionally containing at least one heteroatom selected from the group consisting of oxygen, sulfur and nitrogen, each $R^2$ is the same or different divalent hydrocarbon group containing no ethylenic unsaturation and having up to about 20 carbon atoms and m is 0 to about 8, with hydrogen under hydrogenolysis conditions in the presence of a catalytically effective amount of Group VIII metal catalyst and in the presence of a catalyst poisoning inhibiting amount of a catalyst poisoning inhibitory agent selected from the group consisting of water, except where the mercaptan product contains at least one hydrolyzable silane group, alkanol of from 1 to about 6 carbon atoms, hydrogen sulfide and mixtures thereof to provide organomercaptan product of the general formula (II)

in which $R^1$ and $R^2$ each has one of the aforestated meanings.

Unlike the catalyst sulfidation pretreatment required by the process described in EP 649,837, supra, the process of this invention does not require presulfiding in order to enhance reactivity or inhibit catalyst poisoning.

Under normal conditions, most base metals and precious metal catalysts are poisoned by the formation of sulfides and particularly by alkyl mercaptans. However, it has been discovered that when hydrogenolysis of sulfide is conducted in the presence of a catalyst poisoning inhibitory agent in accordance with this invention, the poisoning effect of the organomercaptan product can be minimized. As a result, both catalytic activity and selectivity increase substantially and high yields of organomercaptan product, e.g., in excess of 98%, can readily be achieved. The hydrogenolysis reaction herein has also been found to occur at more moderate temperatures and pressures. Low catalyst levels can be utilized and still provide completion in less than two hours with high conversion levels and excellent selectivity.

DESCRIPTION OF PREFERRED EMBODIMENTS

The starting sulfide of the present invention can be chosen from among those of the general formula (I):

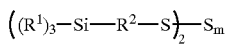  (I)

In sulfide (I), each $R^1$ is the same or different alkyl group of up to about 6 carbon atoms and preferably of up to 4 carbon atoms, e.g., methyl, ethyl, propyl or butyl; aryl group of up to about 10 carbon atoms such as phenyl or naphthyl; alkoxy group of up to about 6 carbon atoms, and preferably up to 4 carbon atoms, e.g., methoxy, ethoxy, propoxy, isopropoxy, butoxy, or isobutoxy; or at least two of $R^1$ and the silicon atom to which they are bonded form a ring system having up to about 12 ring members with no ethylenic unsaturation and optionally containing one or more oxygen, sulfur and/or nitrogen heteroatom members, e.g., the ring system having the structure

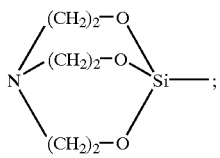

each $R_2$ is a divalent hydrocarbon group containing no ethylenic unsaturation and having up to about 20 carbon atoms, and preferably up to about 12 carbon atoms, e.g., a linear or branched alkylene group such as methylene, ethylene, 1,2-propylene, 1,3-propylene, 2-methyl-1,3-propylene, 3 methyl-1,3-propylene, 3,3-dimethyl-1,3-propylene, ethylidene or isopropylidene, a cycloalkylene group such as cyclohexylene or cycloheptylene, an arylene group such as phenylene, tolylene, xylylene or naphthylene, and m is 0 to 8 and preferably 0 to 4.

Reaction of sulfide (1) with hydrogen to provide organomercaptan product (II) in accordance with the invention can be thought of as proceeding in accordance with the reaction:

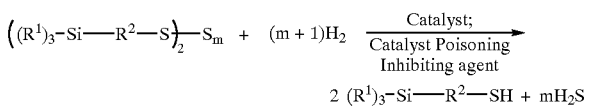

Many examples of sulfide (1) that can be used for preparing organomercaptans in accordance with the present invention and methods for their manufacture are known in the art and include those disclosed in, e.g., U.S. Pat. Nos. 4,072,701; 4,408,064; 5,489,701; 5,466,848; 5,596,116; 5,663,395; 5,663,396; 5,859,275; 5,892,085; 6,147,241; 6,242,652; and, 6,274,755, the contents of which are incorporated by reference herein.

Examples of useful disilylalkyldisulfides of formula (I) include bis[3-(triethoxysilyl)propyl]disulfide[56706-10-6], bis[3-(trimethoxysilyl)propyl]disulfide[35112-74-4], 4,13-diethoxy-4,13-dimethyl-3,14-dioxa-8,9-dithia-4,13-disilahexadecane[188561-27-5], 4,4,13,13-tetraethoxy-6,11-dimethyl-3,14-Dioxa-8,9-dithia-4,13-disilahexadecane [89552-64-7], 8,11-dimethyl-5,5,14,14- tetrapropoxy-4,15-dioxa-9,10-dithia-5,14-disilaoctadecane[170573-44-1], 3,3,12,12-tetramethoxy-6,9-dimethyl-2,13-dioxa-7,8-dithia-3,12-disilatetradecane[170573-43-0], 3,3,12,12-tetramethoxy-4,11-dimethyl-2,13-dioxa-7,8-dithia-3,12-disilatetradecane[182814-38-6], 6,13-dimethyl-5,5,14,14-tetrapropoxy-4,15-dioxa-9,10-dithia-5,14-disilaoctadecane [182814-43-3], bis[3-(tributoxysilyl)propyl]disulfide [42168-82-4] and 5,14-diethyl-3,16-dimethyl-5,14-bis(1-methylpropoxy)-4,15-dioxa-9,10-dithia-5,14-disilaoctadecane.[180003-88-7].

Examples of useful disilylalkyltrisulfides of formula (I) include bis[3-(triethoxysilyl)propyl]trisulfide[56706-11-7], bis[3-(trimethoxysilyl)propyl]trisulfide[40550-17-2], bis[3-(triisopropoxysilyl)propyl]trisulfide[63501-63-3], 3,13-dibutyl-3,13-dimethoxy-2,14-dioxa-7,8,9-trithia-3,13-disilapentadecane[180003-90-1], 3-(tributoxysilyl)propyl 3-(trimethoxysilyl)propyl trisulfide [89552-63-6], (trithiodi-3,1-propanediyl)bis[tris(cyclopentyloxy)-silane[180003-75-2] and 5,21-diethyl-8,8,18,18-tetrakis[(2-ethylhexyl)oxy]-7,19-dioxa-12,13,14-trithia-8,18-disilapentacosane[180003-70-7].

Examples of useful disilylalkyltetrasulfides of formula (I) include bis[3-(trimethoxysilyl)propyl]tetrasulfide[41453-78-5], (tetrathiodi-3,1-propanediyl) bis [tris(isooctyloxy)-silane[180007-08-3], bis[3-triethoxysilyl)propyl] tetrasulfide[40372-72-3], 4,4-diethoxy-15,15-bis (ethoxymethoxy)-3,16,18-trioxa-8,9,10,11-tetrathia-4,15-disilaeicosane[167216-77-5], 6,6,17,17-tetrakis (ethoxymethoxy)-3,5,18,20-tetraoxa-10,11,12,13-tetrathia-6,17-disiladocosane[203457-58-3], 1,1'-(tetrathiodi-3,1-propanediyl)bis-2,8,9-trioxa-5-aza-1-silabicyclo[3.3.3] undecane[68704-61-0], bis[3-(diethoxymethylsilyl)propyl] tetrasulfide[70253-72-4], 2,17-dimethyl4,4,15,15-tetrakis (1-methylethoxy)-3,16-dioxa-8,9,10,11-tetrathia4,15-disilaoctadecane[63501-62-2], 4,4,15,15-tetraethoxy-7,12-dimethyl-3,16-dioxa-8,9,10,11-tetrathia-4,15-disilaoctadecane[57640-08-1], 5,16,16-triethoxy-5-methoxy4,17-dioxa-9,10,11,12-tetrathia-5,16-disilaheneicosane[180003-77-4], 6,6,17,17-tetrabutoxy-5,18-dioxa-10,11,12,13-tetrathia-6,17-disiladocosane[57640-06-9], 3,3,14,14-tetramethoxy-5,12-dimethyl-2,15-dioxa-7,8,9,10-tetrathia-3,14-disilahexadecane[180004-00-6], 3,14-bis(1,1-dimethylethyl)-3,14-dimethoxy-2,15-dioxa-7,8,9,10-tetrathia-3,14-disilahexadecane[243458-27-7], disilatriacontane[57640-07-0], 10,10,21,21-tetrakis (octyloxy)-9,22-dioxa-14,15,16,17-tetrathia-10,21-disilatriacontane[180003-68-3], 10,21-diethoxy-10,21-bis (octyloxy)-9,22-dioxa-14,15,16,17-tetrathia-10,21-disilatriacontane[57640-13-8], 10,10,21-triethoxy-21-(octyloxy)-9,22-dioxa-14,15,16,17-tetrathia-10,21-disilatriacontane[57640-12-7], tetrathiodi-3,1-propanediyl) bis[tris(cyclohexyloxy)-silane[180003-74-1], 3,14-dimethoxy-3,14-diphenyl-2,15-dioxa-7,8,9,10-tetrathia-3,14-disilahexadecane[180003-91-2], 6,17-diethoxy-6,17-diphenyl-5,18-dioxa-10,11,12,13-tetrathia-6,17-disiladocosane[243458-31-3], 14-ethoxy-3,3-dimethoxy-14-phenyl-15-dioxa-7,8,9,10-tetrathia-3,14-disilanonadecane[180003-92-3] and 3,3,14,14-tetramethoxy-6,11-diphenyl-2,15-dioxa-7,8,9,10-tetrathia-3,14-disilahexadecane[137264-06-3].

It is well recognized that the known tetrasulfides are in fact average compositions, including a range from disulfide to octasulfide or higher, and typically are not pure tetrasulfides. Similarly, the useful disulfides and trisulfides can be provided as mixtures, the use of which is also contemplated herein.

The disilylalkyldisulfides are generally preferred due to generation of less by-product $H_2S$, with the methoxy and ethoxydisilylpropyldisulfides being more preferred.

Hydrogenolysis conditions can include a hydrogen pressure from about 100 psig to about 1000 psig and preferably from about 300 psig to about 600 psig, a temperature of from about 160° C. to about 200° C. and preferably from about 180° C. to about 190° C., a reaction time from about 1 hour to about 5 hours and preferably from about 2 hours to about 3 hours.

The catalyst employed in the hydrogenolysis reaction is chosen from amongst the Group VIII metals and is preferably selected from the group consisting of nickel, cobalt, rhodium and ruthenium. The catalyst is preferably one that is supported on any one of numerous known and conventional catalyst support materials, e.g., diatomaceous earth, carbon, silica, alumina, aluminosilicate, and the like.

The amount of catalyst employed can vary widely provided of course, it is a catalytically effective amount. In general, catalyst levels of from about 0.1 wt. % to about 10 wt. % and preferably from about 0.5 wt. % to about 1 wt. % based on the weight of sulfide (I) reactant can be employed with good results.

The catalyst poisoning inhibitory agent of the present can be selected to be water (except where the organomercaptan product contains one or more water sensitive silane groups); an alkanol of from 1 to 6 carbon atoms, preferably selected to match the alkoxy group(s) $R^2$ of the sulfide (I) reactant, and preferably one selected from the group consisting of methanol, ethanol, butanol and isobutanol; and, hydrogen sulfide. Catalyst poisoning inhibitory amounts of the catalyst poisoning inhibitory agent can vary widely and in most cases can be present in the reaction medium at a level of from about 5 wt. % to about 50 wt. % and preferably from about 5 wt. % to about 20 wt. % based on the weight of sulfide (I).

Comparative Examples 1–6 illustrate a catalyzed process for making organomercaptan which omits the use of a catalyst poisoning inhibitory agent and as such, are outside the scope of the present invention. Examples 1–27 are illustrative of the process for preparing organomercaptan of the present invention and clearly demonstrate the advantage of using a catalyst poisoning inhibitory agent. In the tables of data which accompany all of the examples, the following terms have the designated meanings:

"Mercaptan": 3-mercaptopropyltriethoxysilane

"Monosulfide": bis(3-(triethoxysilylpropyl)sulfide

"Disulfide": bis(3-triethoxysilylpropyl)disulfide

"Polysulfide": mixtures of bis[3-(triethoxysilyl)propyl] trisulfide and higher sulfides Comparative Example 1

In a 1 liter Hastelloy C autoclave equipped with a mechanical stirrer, cooling coils and a thermocouple, 591.4 grams of mainly bis(3-triethoxysilylylpropyl)disulfide were combined with 2.0 grams of a 55 wt % nickel catalyst on a kieselguhr support. After purging the autoclave with nitrogen and then hydrogen, the reactor was pressurized to 620 psig with hydrogen and heated to 190° C. while stirring at 1022 rpm. After approximately 180 minutes, the reaction mass was cooled to room temperature and vented to atmospheric pressure. The contents of the reactor were sampled and analyzed by gas chromatography with the following results:

TABLE I

| Time (hrs) | Mercaptan (wt %) | Monosulfide (wt %) | Disulfide (wt %) | Polysulfide (wt %) |
|---|---|---|---|---|
| 1 | 11.2 | 9.5 | 69.4 | 7.3 |
| 2 | 18.4 | 9.0 | 63.0 | 7.2 |
| 3 | 30.7 | 8.5 | 52.6 | 5.0 |

Comparative Examples 2–6

Employing substantially the same procedure as described in Comparative Example 1, additional reactions were carried out with the conditions and results as set forth in Table 2 below.

TABLE 2

| Comp. Ex. | Temp. ° C. | Press psig | Catalyst | Catalyst Amt. (grams) | Disulfide (grams) | Time (minutes) | Mercaptan (wt %) | Monosulfide (wt %) | Disulfide (wt %) | Polysulfide (wt %) |
|---|---|---|---|---|---|---|---|---|---|---|
| 2 | 100 | 1400 | 5% Pd/C | 4 | 637 | 60 | 1.9 | 9.8 | 89.1 | 1.2 |
| 3 | 190 | 300 | 55% Ni/silica (G-49B) | 5 | 547 | 60 | 10.8 | 8.33 | 65.4 | 9.7 |
|  |  |  |  |  |  | 120 | 39.1 | 7.94 | 44.9 | 1.6 |
| 4 | 190 | 1000 | 55% Ni/silica (G-49B) | 5 | 503 | 60 | 17.8 | 8.69 | 60.2 | 8 |
|  |  |  |  |  |  | 120 | 66.5 | 7.9 | 20.7 | 0 |
| 5 | 190 | 600 | 55% Ni/silica (G-49B) | 5 | 502 | 60 | 13.6 | 8.9 | 62.5 | 7.3 |
|  |  |  |  |  |  | 120 | 30.7 | 7.8 | 49.8 | 3 |
|  |  |  |  |  |  | 180 | 44 | 7.5 | 36.2 | 0 |
| 6 | 200 | 600 | 55% Ni/silica (G-49B) | 5 | 490 | 60 | 18.2 | 8.4 | 62 | 5.7 |
|  |  |  |  |  |  | 120 | 39 | 8 | 45.9 | 1.6 |
|  |  |  |  |  |  | 180 | 57 | 7.88 | 28.7 | 0 |

As the data in Tables 1 and 2 of Comparative Examples 1–6 amply show, absence of a catalyst poisoning inhibitory agent resulted in much larger amounts of disulfide product relative to the amounts of mercaptan produced.

EXAMPLE 1

In a 1 liter Hastelloy C autoclave equipped with a mechanical stirrer, cooling coils and a thermocouple, 360.2 grams of mainly bis(3-triethoxysilylypropyl)disulfide were combined with 40.7 grams ethanol and 2.0 grams of a 55 wt % nickel catalyst on a kieselguhr support. After purging the autoclave with nitrogen and then hydrogen, the reactor was pressurized to 624 psig with hydrogen and heated to 190° C. while stirring at 1007 rpm. After approximately 180 minutes, the reaction mass was cooled to room temperature and vented to atmospheric pressure. The contents of the reactor were sampled and analyzed by gas chromatography with the following results:

TABLE 3

| Time (hrs) | Mercaptan (wt %) | Monosulfide (wt %) | Disulfide (wt %) | Polysulfide (wt %) |
|---|---|---|---|---|
| 1 | 31.7 | 7.5 | 43.6 | 3.4 |
| 2 | 55.86 | 6.87 | 22.24 | 1 |
| 3 | 77.33 | 6.46 | 0 | 0 |

EXAMPLE 2

In a 1 liter Hastelloy C autoclave equipped with a mechanical stirrer, cooling coils and a thermocouple, 310.3 grams of mainly bis(3-triethoxysilylpropyl)disulfide were combined with 5.0 grams of a 55 wt % nickel catalyst on a kieselguhr support. After purging the autoclave with nitrogen and then hydrogen, the reactor was charged with 35 grams of hydrogen sulfide, pressurized to 615 psig with hydrogen and heated to 190° C. while stirring at 1087 rpm. After approximately 150 minutes, the reaction mass was cooled to room temperature and vented to atmospheric pressure. The contents of the reactor were sampled and analyzed by gas chromatography with the following results:

TABLE 4

| Time (hrs) | Mercaptan (wt %) | Monosulfide (wt %) | Disulfide (wt %) | Polysulfide (wt %) |
|---|---|---|---|---|
| 1 | 23.4 | 8.1 | 56.6 | 3.4 |
| 2 | 55.38 | 7.3 | 27.4 | 0.6 |
| 2.5 | 73.5 | 6.7 | 8.5 | 0 |

EXAMPLES 3–25

Employing substantially the same procedures as described in Examples 1–3, additional reactions were carried out employing ethanol as the catalyst poisoning inhibitory agent with the conditions and results as set forth in Table 5 below:

In each of Examples 1–25, much higher levels of mercaptan relative to disulfide were obtained compared with those obtained in Comparative Examples 1–6. In some cases, the greater levels of mercaptan manifested themselves after only 60 minutes of reaction time and in other cases, the highest levels of mercaptan relative to disulfide were achieved only after several hours of reaction. The foregoing data convincingly demonstrate the advantage of employing a catalyst poisoning inhibitory agent in accordance with the present invention when it is desired to maximize the amount of mercaptan produced relative to disulfide and other sulfide products.

What is claimed is:

1. Process for preparing an organomercaptan which comprises reacting a sulfide of the general formula (I)

$$\left((R^1)_3-Si-R^2-S\right)_2-S_m \tag{I}$$

in which each $R^1$ is the same or different alkyl group of up to about 6 carbon atoms, aryl group of up to about 10 carbon atoms or alkoxy group of up to about 6 carbon atoms, or at least two of $R^1$ and the silicon atom to which they are bonded form a ring system having up to about 12 ring members with no ethylenic unsaturation and optionally containing one or more heteroatoms selected from the group

TABLE 5

| Ex. | Temp. ° C. | Press psig | Catalyst | Catalyst Amt. (grams) | Disulfide (grams) | Ethanol (grams) | Time (minutes) | Mercaptan (wt %) | Monosulfide (wt %) | Disulfide (wt %) | Polysulfide (wt %) |
|---|---|---|---|---|---|---|---|---|---|---|---|
| 3 | 190 | 1400 | 5% Rh/C | 6 | 303 | 269 | 90 | 41.3 | 2.9 | 0 | 0 |
| 4 | 190 | 1400 | 5% Pt/C | 6 | 381 | 262 | 60 | 8.2 | 4.1 | 29.9 | 4.5 |
| 5 | 190 | 1400 | 5% Pd/C | 6 | 359 | 324 | 60 | 7.4 | 4.1 | 32.5 | 4.1 |
| 6 | 190 | 1400 | 5% Rh/C | 6 | 251 | 250 | 60 | 39.7 | 3 | 2.5 | 0 |
| 7 | 190 | 1400 | PtS/C | 6 | 250 | 259 | 60 | 5.2 | 3.9 | 18.1 | 4.9 |
| 8 | 190 | 1400 | 10% Pd/C | 6 | 255 | 254 | 60 | 7.1 | 3.6 | 27.5 | 3.9 |
| 9 | 190 | 1400 | 5% Ru/C | 1 | 263 | 267 | 60 | 8.4 | 3.7 | 28.7 | 3.1 |
|  |  |  |  |  |  |  | 120 | 18.1 | 3.8 | 26.3 | 0.67 |
| 10 | 190 | 600 | 5% Rh/C | 6 | 251 | 254 | 120 | 39.5 | 3.1 | 0 | 0 |
| 11 | 100 | 600 | 5% Rh/C | 3 | 277 | 251 | 120 | 44 | 3.7 | 0 | 0 |
| 12 | 190 | 600 | 5% Rh/C | 3 | 380 | 125 | 120 | 52.6 | 5.8 | 15.7 | 0 |
| 13 | 190 | 300 | 5% Rh/C | 3 | 250 | 250 | 120 | 47.4 | 3.6 | 0 | 0 |
| 14 | 190 | 300 | 10% Ru/C | 3 | 250 | 250 | 60 | 20.2 | 3.4 | 17.7 | 1.8 |
|  |  |  |  |  |  |  | 120 | 33.5 | 3.5 | 9.9 | 0 |
| 15 | 190 | 300 | 5% Ru/C | 3 | 250 | 250 | 60 | 27.1 | 4.6 | 24 | 0 |
|  |  |  |  |  |  |  | 120 | 28.6 | 4.3 | 18.6 | 0 |
| 16 | 190 | 300 | 5% Ru/C Pre-Activated | 3 | 274 | 270 | 120 | 30.9 | 3.4 | 10.4 | 0 |
|  |  |  |  |  |  |  | 150 | 43.4 | 2.6 | 0 | 0 |
| 17 | 190 | 300 | CoO/MoO3 on Alumina | 10 | 298 | 249 | 105 | 5.4 | 4.4 | 33 | 0 |
|  |  |  |  |  |  |  | 150 | 39.9 | 6.7 | 20.8 | 5.3 |
| 18 | 190 | 600 | 33% Co/alumina | 5 | 361 | 43 | 60 | 15.4 | 7.1 | 53.2 | 5.7 |
|  |  |  |  |  |  |  | 120 | 50 | 6.6 | 25 | 0.7 |
|  |  |  |  |  |  |  | 150 | 75.7 | 6.3 | 3.7 | 0 |
| 19 | 190 | 300 | 55% Ni/silica (G-49B) | 5 | 256 | 251 | 60 | 24.9 | 4.33 | 16.5 | 1.5 |
|  |  |  |  |  |  |  | 120 | 44.5 | 5.5 | 0 | 0 |
| 20 | 190 | 600 | 55% Ni/silica (G-49B) | 5 | 400 | 100 | 60 | 39.6 | 6.27 | 23.6 | 1.5 |
|  |  |  |  |  |  |  | 120 | 69.2 | 6.7 | 0 | 0 |
| 21 | 190 | 600 | 55% Ni/silica (G-49B) | 5 | 415 | 46 | 60 | 44.4 | 7.59 | 32.5 | 1.8 |
|  |  |  |  |  |  |  | 90 | 70.8 | 8.2 | 5.5 | 0 |
|  |  |  |  |  |  |  | 120 | 76.8 | 9.5 | 0 | 0 |
| 22 | 190 | 300 | 55% Ni/silica (G-49B) | 5 | 498 | 53 | 60 | 18.2 | 7.6 | 51.4 | 5.7 |
|  |  |  |  |  |  |  | 120 | 35.3 | 7.85 | 39.1 | 2.5 |
|  |  |  |  |  |  |  | 180 | 55.9 | 8 | 19.4 | 0 |
| 23 | 190 | 600 | 55% Ni/silica (G-49B) | 5 | 360 | 41 | 60 | 31.7 | 7.5 | 43.6 | 3.4 |
|  |  |  |  |  |  |  | 120 | 55.8 | 7.7 | 22.2 | 0.97 |
|  |  |  |  |  |  |  | 180 | 77.3 | 8.8 | 0.6 | 0 |
| 24 | 190 | 600 | Raney ™ Nickel 4200 | 5 | 357 | 41 | 60 | 11 | 7.56 | 56.6 | 6.3 |
| 25 | 190 | 600 | 55% Ni/silica (G-49B) | 5 | 359 | 41 | 120 | 76.7 | 5.1 | 0 | 0 | consisting of oxygen, sulfur and nitrogen, each $R^2$ is the same or different divalent hydrocarbon group containing no ethylenic unsaturation and having up to about 20 carbon atoms and m is 0 to about 8, with hydrogen under hydrogenolysis conditions in the presence of a catalytically effective amount of Group VIII metal catalyst and in the presence of a catalyst poisoning inhibiting amount of a catalyst poisoning inhibitory agent selected from the group consisting of water, except where the mercaptan product contains at least one hydrolyzable silane group, alkanol of from 1 to about 6 carbon atoms, hydrogen sulfide and mixtures thereof to provide organomercaptan product of the general formula (II)

$(R^1)_3—Si—R^2—SH$ (II)

in which $R^1$ and $R^2$ each has one of the aforestated meanings.

2. The process of claim 1 wherein at least one $R^1$ is an alkyl group selected from the group consisting of methyl, ethyl, propyl and butyl.

3. The process of claim 1 wherein at least one $R^1$ is a phenyl group.

4. The process of claim 1 wherein at least one $R^1$ is an alkoxy group selected from the group consisting of methoxy, ethoxy, propoxy or butoxy.

5. The process of claim 1 wherein each $R^2$ is the same or different divalent alkylene radical of up to about 12 carbon atoms.

6. The process of claim 5 wherein each $R^2$ is the same or different divalent alkylene radical selected from the group consisting of methylene, ethylene, 1,2-propylene, 2-methyl-1,3-propylene, 3-methyl-1,3-propylene, 3,3-dimethyl-1,3-propylene, ethylidene or isopropylene, cyclohexylene, cycloheptylene, phenylene, tolylene, xylylene and naphthylene.

7. The process of claim 1 wherein m is 0 to 4.
8. The process of claim 2 wherein m is 0 to 4.
9. The process of claim 3 wherein m is 0 to 4.
10. The process of claim 4 wherein m is 0 to 4.
11. The process of claim 5 wherein m is 0 to 4.
12. The process of claim 6 wherein m is 0 to 4.
13. The process of claim 1 wherein sulfide (I) is a disilylalkyldisulfide selected from the group consisting of bis[3-(triethoxysilyl)propyl]disulfide, bis[3-(trimethoxysilyl)propyl]disulfide, 4,13-diethoxy-4,13-dimethyl-3,14-dioxa-8,9-dithia- 4,13-disilahexadecane, 4,4,13,13-tetraethoxy-3,14-dioxa-8,9-dithia-4,13-disilahexadecane, 8,11-dimethyl-5,5,14,14- tetrapropoxy-4,15-dioxa-9,10-dithia-5,14-disilaoctadecane, 3,3,12,12-tetramethoxy-6,9-dimethyl-2,13-dioxa-7,8-dithia-3,12-disilatetradecane, 3,3,12,12-tetramethoxy-4,11-dimethyl-2,13-dioxa-7,8-dithia-3,12-disilatetradecane, 6,13-dimethyl-5,5,14,14-tetrapropoxy-4,15-dioxa-9,10-dithia-5,14-disilaoctadecane, bis[3-(tributoxysilyl)propyl]disulfide and 5,14-diethyl-3,16-dimethyl-5,14-bis(1-methylpropoxy)-4,15-dioxa-9,10-dithia-5,14-disilaoctadecane.

14. The process of claim 1 wherein sulfide (I) is a disilylalkyltrisulfide selected from the group consisting of bis[3-(triethoxysilyl)propyl]trisulfide, bis[3-(trimethoxysilyl)propyl]trisulfide, bis[3-(triisopropoxysilyl) propyl] trisulfide, 3,13-dibutyl-3,13-dimethoxy-2,14-dioxa-7,8,9-trithia-3,13-disilapentadecane, 3-(tributoxysilyl) propyl 3-(trimethoxysilyl)propyl trisulfide, (trithiodi-3,1-propanediyl)bis[tris(cyclopentyloxy)-silane and 5,21-diethyl-8,8,18,18-tetrakis[(2-ethylhexyl)oxy]-7, 19-dioxa-12,13,14-trithia-8,18-disilapentacosane.

15. The process of claim 1 wherein sulfide (I) is a disilylalkyltetrasulfide selected from the group consisting of bis[3-(trimethoxysilyl)propyl]tetrasulfide, (tetrathiodi-3,1-propanediyl)bis[tris(isooctyloxy)-silane, bis[3-triethoxysilyl)propyl] tetrasulfide, 4,4-diethoxy-15,15-bis(ethoxymethoxy)-3,16,18-trioxa-8,9,10,11-tetrathia4,15-disilaeicosane, 6,6,17,17-tetrakis(ethoxymethoxy)-3,5,18,20-tetraoxa-10,11,12,13-tetrathia-6,17-disiladocosane, 1,1'-(tetrathiodi-3,1-propanediyl)bis-2,8,9-trioxa-5-aza-1-silabicyclo[3.3.3]undecane, bis[3-(diethoxymethylsilyl) propyl]tetrasulfide, 2,17-dimethyl-4,4,15,15-tetrakis(1-methylethoxy)-3,16-dioxa-8,9,10,11-tetrathia-4,15-disilaoctadecane, 4,4,15,15-tetraethoxy-7,12-dimethyl-3,16- dioxa-8,9,10,11-tetrathia-4,15-disilaoctadecane, 5,16,16,-triethoxy-5-methoxy4,17-dioxa-9,10,11,12-tetrathia-5,16-disilaheneicosane, 6,6,17,17-tetrabutoxy-5,18-dioxa-10,11,12,13-tetrathia-6,17-disiladocosane, 3,3,14,14-tetramethoxy-5,12-dimethyl-2,15-dioxa-7,8,9,10-tetrathia-3,14-disilahexadecane, 3,14-bis(1,1-dimethylethyl)-3,14-dimethoxy-2,15-dioxa-7,8,9,10-tetrathia-3,14-disilahexadecane, disilatriacontane, 10,10,21,21-tetrakis (octyloxy)-9,22-dioxa-14,15,16,17-tetrathia-10,21-disilatriacontane, 10,21-diethoxy-10,21-bis(octyloxy)-9,22-dioxa-14,15,16,17-tetrathia-10,21-disilatriacontane, 10,10,21-triethoxy-21-(octyloxy)-9,22-dioxa-14,15,16,17-tetrathia-10,21-disilatriacontane, tetrathiodi-3,1-propanediyl)bis[tris(cyclohexyloxy)-silane, 3,14-dimethoxy-3,14-diphenyl-2,15-dioxa-7,8,9,10-tetrathia-3,14-disilahexadecane, 6,17-diethoxy-6,17-diphenyl-5,18-dioxa-10,11,12,13-tetrathia-6,17-disiladocosane, 14-ethoxy-3,3-dimethoxy-14-phenyl-2,15-dioxa-7,8,9,10-tetrathia-3,14-disilanonadecane and 3,3,14,14-tetramethoxy-6,11-diphenyl-2,15-dioxa-7,8,9,10-tetrathia-3,14-disilahexadecane.

16. The process of claim 1 wherein the hydrogenolysis conditions include a hydrogen pressure of from about 300 psig to about 600 psig, a temperature of from about 160° C. to about 190° C. and a reaction time of from about 2 hours to about 5 hours.

17. The process of claim 1 wherein the Group VIII metal catalyst is nonsupported or supported and contains at least one metal selected from the group consisting of nickel, cobalt, rhodium and ruthenium.

18. The process of claim 1 wherein the catalyst is present at from about 1 to about 10 weight percent by weight of sulfide (I).

19. The process of claim 1 wherein the alkanol is selected from the group consisting of methanol, ethanol, propanol, isopropanol, butanol and isobutanol.

20. The process of claim 1 wherein the catalyst poisoning inhibitory agent is present in an amount of from about 5 to about 50 weight percent by weight of sulfide (I).

* * * * *

UNITED STATES PATENT AND TRADEMARK OFFICE
CERTIFICATE OF CORRECTION

PATENT NO.    : 6,433,206 B1
DATED         : August 13, 2002
INVENTOR(S)   : Gedon et al.

It is certified that error appears in the above-identified patent and that said Letters Patent is hereby corrected as shown below:

<u>Title page,</u>
Item [22], Filed, please delete "November 15, 2001" and insert correct Filing Date
-- November 5, 2001 --

Signed and Sealed this

Twenty-first Day of January, 2003

JAMES E. ROGAN
*Director of the United States Patent and Trademark Office*